(12) United States Patent
Watt et al.

(10) Patent No.: US 12,127,774 B2
(45) Date of Patent: Oct. 29, 2024

(54) K-WIRE IMPLANTS FOR FRACTURES

(71) Applicant: DEPUY SYNTHES PRODUCTS, INC., Raynham, MA (US)

(72) Inventors: Philip Watt, New Holland, PA (US); Kory Smith, Exton, PA (US); Jeffrey Loftus-Vergari, Media, PA (US); Danielle Rossi, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 18/182,913

(22) Filed: Mar. 13, 2023

(65) Prior Publication Data

US 2023/0248407 A1 Aug. 10, 2023

Related U.S. Application Data

(63) Continuation of application No. 17/327,132, filed on May 21, 2021, now Pat. No. 11,633,221.

(Continued)

(51) Int. Cl.
*A61B 17/88* (2006.01)
*A61B 17/72* (2006.01)
(Continued)

(52) U.S. Cl.
CPC .......... *A61B 17/88* (2013.01); *A61B 17/7233* (2013.01); *A61B 17/808* (2013.01); *A61B 17/848* (2013.01); *A61B 17/8605* (2013.01); *A61B 17/861* (2013.01); *A61B 2017/564* (2013.01)

(58) Field of Classification Search
CPC .......... A61B 17/0642; A61B 2017/681; A61B 17/7233; A61B 17/80; A61B 17/8004; A61B 17/8061; A61B 17/809; A61B 17/842; A61B 17/848; A61B 17/8605; A61B 17/8695; A61B 17/88
See application file for complete search history.

(56) References Cited

U.S. PATENT DOCUMENTS 5,306,275 A * 4/1994 Bryan ................ A61B 17/7055
606/267
5,380,325 A * 1/1995 Lahille ............... A61B 17/7041
403/294

(Continued)

FOREIGN PATENT DOCUMENTS

| CN | 2006017507 A2 | 2/2006 |
|---|---|---|
| CN | 101642290 A | 2/2010 |

(Continued)

OTHER PUBLICATIONS

Kim, J. Y., Lee, Y. H., Gong, H. S., Lee, S. L., Lee, S. K., amp; Baek, G. H. (2013). Use of Kirschner Wires With Eyelets for Tension Band Wiring of Olecranon Fractures. The Journal of Hand Surgery, 8, 1762-1767. (Year: 2013).

*Primary Examiner* — Larry E Waggle, Jr.
(74) *Attorney, Agent, or Firm* — Kramer & Amado, P.C.

(57) ABSTRACT

A slotted washer configured to secure a K-wire to a native bone, including: an upper arm with a screw hole; a lower arm with a screw hole; a connector connecting the upper arm with the lower arm; and a K-wire opening between the connector, lower arm, and upper arm configured to receive and compress the K-wire.

9 Claims, 7 Drawing Sheets

Related U.S. Application Data (60) Provisional application No. 63/032,249, filed on May 29, 2020.

(51) Int. Cl.
*A61B 17/80* (2006.01)
*A61B 17/84* (2006.01)
*A61B 17/86* (2006.01)
*A61B 17/56* (2006.01)

(56) References Cited

U.S. PATENT DOCUMENTS

| | | | |
|---|---|---|---|
| 5,941,878 | A | 8/1999 | Medoff |
| 6,379,359 | B1 | 4/2002 | Dahners |
| 6,730,090 | B2 | 5/2004 | Orbay |
| 7,862,593 | B2 * | 1/2011 | Clement ............ A61B 17/7041 606/310 |
| 8,740,903 | B2 | 6/2014 | Bottlang |
| 10,004,603 | B2 | 6/2018 | Appenzeller |
| 10,016,226 | B2 * | 7/2018 | Fening ................ A61B 17/707 |
| 10,543,026 | B2 | 1/2020 | Kim |
| 10,617,454 | B2 * | 4/2020 | Orbay ................ A61B 17/8057 |
| 10,973,550 | B2 * | 4/2021 | Wurapa .............. A61B 17/6475 |
| 2003/0187432 | A1 * | 10/2003 | Johnson ................ A61B 17/66 606/59 |
| 2004/0111090 | A1 | 6/2004 | Laurence |
| 2007/0233113 | A1 | 10/2007 | Kaelblein |
| 2008/0058805 | A1 * | 3/2008 | Stuart ................... A61B 17/705 606/86 A |
| 2011/0009912 | A1 | 1/2011 | Gonzalez-Hernandez |
| 2012/0290016 | A1 | 11/2012 | Kumar |
| 2013/0110110 | A1 * | 5/2013 | Waisman ........... A61B 17/6458 606/59 |
| 2014/0074174 | A1 | 3/2014 | Schacherer |
| 2015/0164355 | A1 | 6/2015 | Marina |
| 2016/0199113 | A1 | 7/2016 | Penzimer |
| 2018/0160612 | A1 | 6/2018 | Li |
| 2020/0015865 | A1 | 1/2020 | Bradley |

FOREIGN PATENT DOCUMENTS

| | | |
|---|---|---|
| CN | 201642290 U | 11/2010 |
| CN | 102327144 A | 1/2012 |
| CN | 2015164355 A1 | 10/2015 |
| CN | 2018160612 A1 | 9/2018 |
| CN | 101909350 B1 | 10/2018 |
| CN | 209529311 U | 10/2019 |

* cited by examiner

FIG. 7E ically to a K-wire implants for fractures.

K-WIRE IMPLANTS FOR FRACTURES

CROSS-REFERENCE TO RELATED APPLICATIONS

This application claims benefit to U.S. patent application Ser. No. 17/327,132, filed on May 21, 2021 and U.S. Provisional Patent Application No. 63/032,249 filed on May 29, 2020, the contents of both which are hereby incorporated by reference for all purposes as if fully set forth herein.

TECHNICAL FIELD

Various exemplary embodiments disclosed herein relate generally to a K-wire implants for fractures.

BACKGROUND

K-wires are sharpened, smooth pins that are widely used in orthopedic surgery as well as other types of surgery. They are often made of stainless steel. K-wires come in a variety of sizes and are used to hold bone fragments together. K-wires may be driven into the bone (sometimes through the skin) using a power or hand drill.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a slotted washer configured to secure a K-wire to a native bone, including: an upper arm with a screw hole; a lower arm with a screw hole; a connector connecting the upper arm with the lower arm; and a K-wire opening between the connector, lower arm, and upper arm configured to receive and compress the K-wire.

Various embodiments are described, further including a window adjacent the K-wire opening configured to provide a view of the K-wire during insertion into the K-wire opening.

Various embodiments are described, wherein the window is in the upper arm.

Various embodiments are described, wherein the window is in the upper arm and the lower arm.

Various embodiments are described, wherein the screw hole of the upper arm includes frustoconical shaped rim.

Various embodiments are described, wherein the width of K-wire opening is greater than the width of a gap between the upper arm and the lower arm.

Various embodiments are described, method for implanting a K-wire using the slotted washer, including: reducing a bone fragment to a native bone; driving the K-wire through the bone fragment into the native bone; backing the K-wire out of the bone; bending the K-wire to conform to the native bone so that plate is flush to the native bone; pushing the bent K-wire back into the bone; selecting a location to secure the K-wire to the native bone; cutting off an excess length of the K-wire; placing the slotted washer over the cut K-wire; and inserting a screw in the screw hole to secure the slotted washer and the K-wire to the native bone.

Various embodiments are described, wherein the slotted washer further includes a window adjacent the K-wire opening configured to provide a view of the K-wire during insertion into the K-wire opening.

Various embodiments are described, wherein the window is in the upper arm.

Various embodiments are described, wherein the window is in the upper arm and the lower arm.

Various embodiments are described, further including positioning slotted washer along the K-wire so that the end of the K-wire is visible in the window.

Various embodiments are described, further including positioning slotted washer along the K-wire so that the K-wire extends through the window.

Various embodiments are described, wherein the screw hole of the upper arm includes frustoconical shaped rim.

Various embodiments are described, wherein the width of K-wire opening is greater than the width of a gap between the upper arm and the lower arm.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Dorsal and volar rim fractures of the distal radius are difficult to fix, because they include small fragments and have fragment displacing forces from the wrist (bone and ligamentous) acting on the fragments. These fractures must be fixed to prevent ongoing dislocation of the wrist. K-wires have been used to capture and fix these fractures by surgeons. For example after the fracture has been reduced, the surgeon may drive a K-wire into the bone fragment using a driver. The K-wire may then be bent down along the bone long axis and then secured to the bone using for example a plate.

Various new implants will be described herein that will ease implantation and reliably fix the K-wires. First, four different embodiments of K-wire with an integrated plate structure will be described. Next a donut shaped washer for capturing and securing the K-wire is disclosed. Further, a screw with a channel is disclosed that has a head shaped to capture and secure the K-wire. Finally, embodiments of a slotted washer are disclosed that captures and secures the K-wire. While these embodiments are described for use with volar rim factures, the embodiments may be adapted and used in various other locations and applications.

FIGS. 1A, 1B, 1C, 1D, and 1E illustrate perspective, top, side, end, and cross-sectional (through the plate) views respectively of a first embodiment of a K-wire with an integrated plate. The K-wire 100 may include a driver pin 104, an implant pin 110, and a plate 102. The driver pin 104 has a length sufficient to enable a driver to engage the driver pin 104 as well as to allow it to be used to help bend the K-wire 100 into position. The diameter of the driver pin 104 may be greater than the diameter of the implant pin 110, but in some embodiments they may have the same diameter. In some examples, the diameters of the driver pin 104 and implant pin 110 may respectively be 1.6 mm and 1.2 mm, 2.0 mm and 1.6 mm, or 2.0 and 1.2 mm. This difference may help to clearly differentiate between the driver pin 104 and the implant pin 110 during use. Also, the increased diameter of the driving portion 104 may improve stability when the K-wire 100 is driven into the bone. Also the diameter of the driving portion may be selected to be the same or less than the thickness of the plate 102 so that the K-wire has as low profile as possible.

The implant pin 110 may have a distal end 114 that is sharp, pointed, and/or chiseled so that it can be driven into the bone when rotated by the driver. As discussed above the diameter of the implant pin 110 may be smaller than the diameter of the driver pin 104. The diameter will be sufficient to provide the structural strength and integrity for the implant pin 110 to hold the fractured bone in place, but also to be able to be bent into a desired shape to be secured to the bone. The driver pin 104 and the implant pin 110 are substantially colinear to allow the K-wire 100 to be driving into the bone.

The plate 102 is attached between the driver pin 104 and the implant pin 110. The plate 102 is shown as round, but may take on other shapes as well. The plate 102 has a screw hole 106 configured to receive a screw to secure the plate 102 to the bone. Further, the hole 106 may have a frustoconical shaped rim 108 that is configured to mate with the head of the screw used to secure the plate 102 to the bone. This rim 108 facilitates a more secure fixation to the bone as well as leading to a lower profile installation as the screw head may be below the upper edge of the rim 108.

FIGS. 2A, 2B, 2C, 2D, and 2E illustrate perspective, top, side, end, and cross-sectional (through the plate) views respectively of a second embodiment of a K-wire with an integrated plate. The K-wire 200 may include a driver pin 204, an implant pin 210, and a plate 202. The driver pin 204 has a length sufficient to enable a driver to engage the driver pin 204 as well as to allow it to be used to help bend the K-wire 200 into position. The diameter of the driver pin 204 may be greater than the diameter of the implant pin 210. In some examples, the diameters may be 1.6 mm and 1.2 mm, 2.0 mm and 1.6 mm, or 2.0 and 1.2 mm. This difference may help clearly differentiate between the driver pin 204 and the implant pin 210 during use. Also, the increased diameter of the driver pin 204 may improve stability when the K-wire 200 is driven into the bone. Also the diameter of the driving portion may be selected to be the same or less than the thickness of the plate 202 so that the K-wire has as low profile as possible.

The implant pin 210 may have a distal end 214 that is sharp, pointed, and/or chiseled so that it can be driven into the bone when rotated by the driver. As discussed above the diameter of the implant pin 210 may be smaller than the diameter of the driver pin 204. The diameter will be sufficient to provide the structural strength and integrity for the implant pin 210 to hold the fractured bone in place, but also to be able to be bent into a desired shape to be secured to the bone.

The plate 202 is attached between the driver pin 204 and the implant pin 210. The plate 202 is shown as generally rectangular, but may take on other shapes as well. The plate 202 has two screw holes 206 and 207 configured to receive screws to secure the plate 202 to the bone. Further, the holes 206, 207 may have frustoconical shaped rims 208, 209 that are configured to mate with the head of the screw used to secure the plate 202 to the bone. These rims 208, 209 facilitate a more secure fixation to the bone as well as leading to a lower profile installation as the screw head may be below the upper edge of the rims 208, 209. The driver pin 204 and the implant pin 210 are substantially colinear to allow the K-wire 200 to be driven into the bone.

Figure 1A:
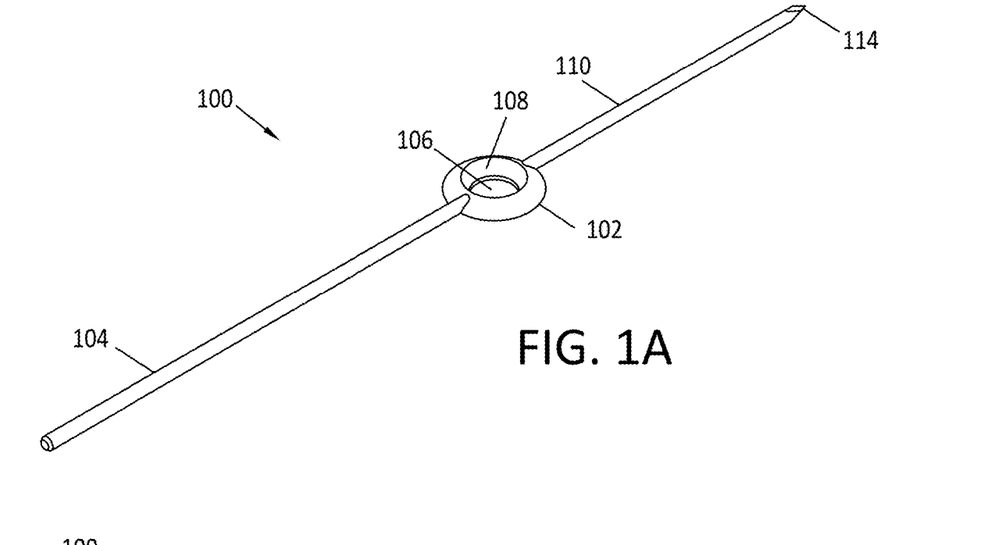
FIGS. 1A, 1B, 1C, 1D, and 1E illustrate perspective, top, side, end, and cross-sectional (through the plate) views respectively of a first embodiment of a K-wire with an integrated plate.
Figure 1B:
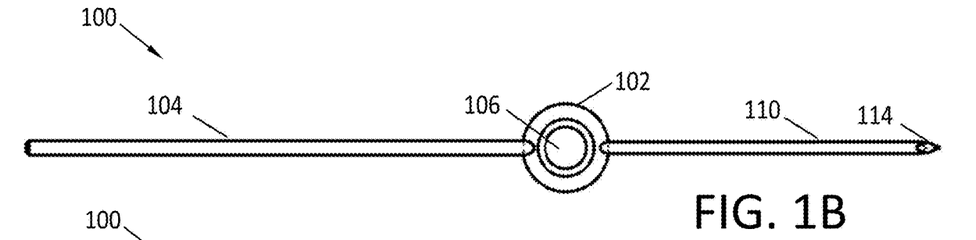
Figure 1C:
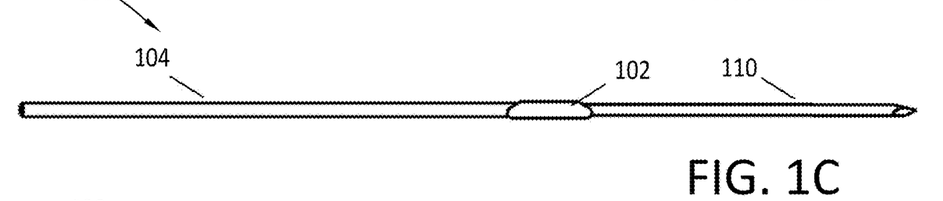
Figure 1D:
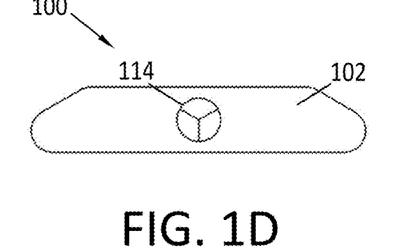
Figure 1E:
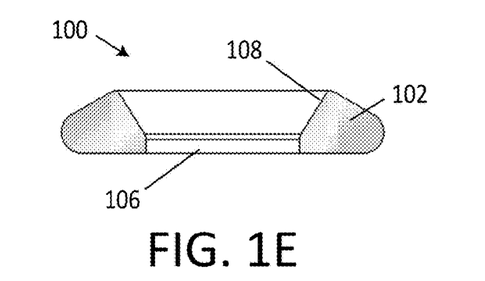
Figure 2A:
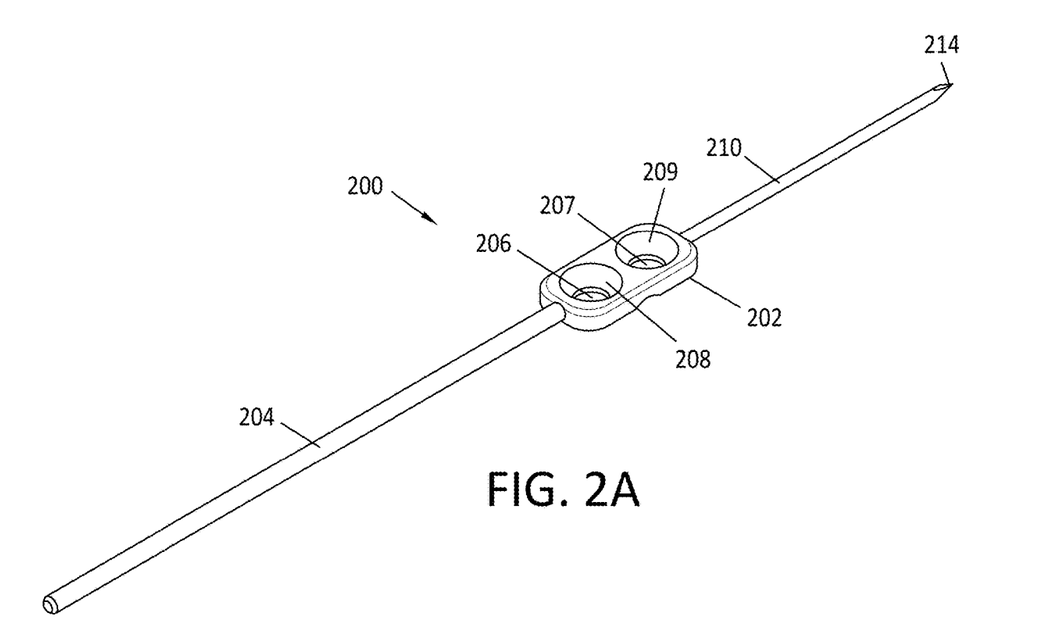
FIGS. 2A, 2B, 2C, 2D, and 2E illustrate perspective, top, side, end, and cross-sectional (through the plate) views respectively of a second embodiment of a K-wire with an integrated plate.
Figure 2B:
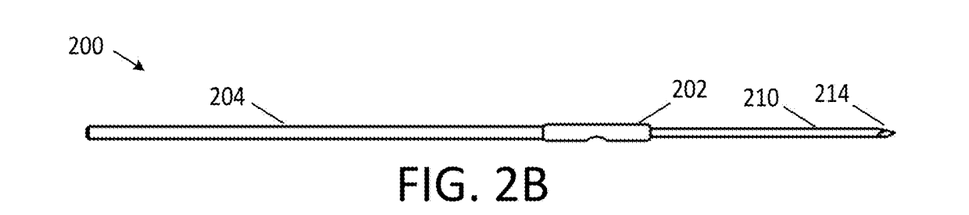
Figure 2C:
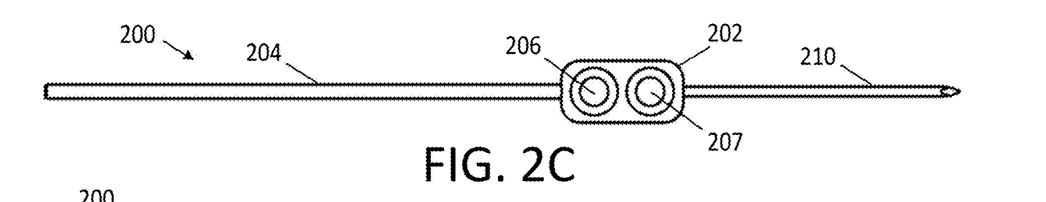
Figure 2D:
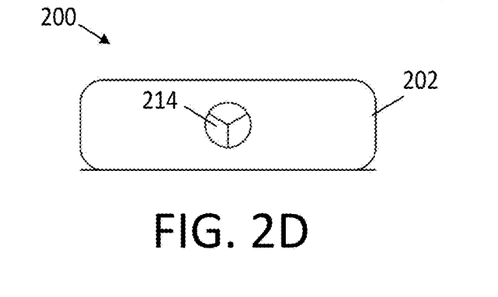
Figure 2E:
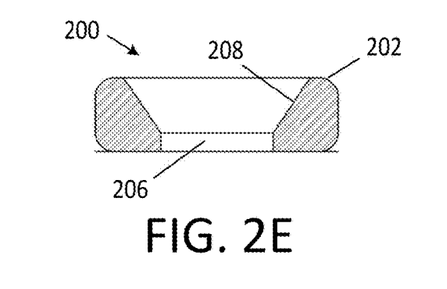

A method for using the K-wires 100, 200 will now be described. First, the bone fragment is reduced to the native bone. The K-wire 100, 200 is then attached to a driver, and the K-wire 100, 200 is driven through the bone fragment into the native bone. Then the K-wire 100, 200 may be backed out of the bone, for example by 5-10 mm. The K-wire 100, 200 is then bent to conform to the native bone so that the plate 102, 202 is flush to the native bone. Next, the bent K-wire 100, 200 is pushed back into the bone to be flush with the bone. The driver pin 104, 204 may then be cut off. Finally, a screw(s) is inserted into the plate 102, 202 to fix the plate 102, 202 and the K-wire 100, 200 to the bone.

FIGS. 3A, 3B, 3C, 3D, and 3E illustrate perspective, top, side, end, and cross-sectional (through the plate) views respectively of a third embodiment of a K-wire with an integrated plate. The K-wire 300 may include a driver tab 304, implant pins 310, 312, and a plate 302. The driver tab 304 has a length sufficient to enable a driver to engage the driver tab 304 as well as to allow it to be used to help bend the K-wire 300 into position. In alternative embodiments, the K-wire 300 may not include driver tab 304, but instead a driver may engage the plate 302 directly for insertion.

The implant pins 310, 312 may have distal ends 314, 316 that are sharp, pointed, and/or chiseled so that they can be driven into the bone. The diameter of the implant pins 310, 312 will be sufficient to provide the structural strength and integrity for the implant pins 310, 312 to hold the fractured bone in place, but also to be able to be bent into a desired shape to be secured to the bone. In some embodiments, the implant pins 310, 312 may be of different lengths that may facilitate implanting the K-wire 300.

The plate 302 is attached between the driver tab 304 and the implant pins 310, 312. The plate 302 is shown as generally rectangular, but may take on other shapes as well. The plate 302 has a screw hole 306 configured to receive a screw to secure the plate 302 to the bone. Further, the hole 306 may have a frustoconical shaped rim 308 that is configured to mate with the head of the screw used to secure the plate 302 to the bone. This rim 308 facilitates a more secure fixation to the bone as well as leading to a lower profile installation as the screw head may be below the upper edge of the rim 308. The plate 302 is designed to be as low profile as possible.

FIGS. 4A, 4B, 4C, 4D, and 4E illustrate perspective, top, side, end, and cross-sectional (through the plate) views respectively of a fourth embodiment of a K-wire with an integrated plate. The K-wire 400 may include a driver tab 404, implant pins 410, 412, and a plate 402. The driver tab 404 has a length sufficient to enable a driver to engage the driver tab 404 as well as to allow it to be used to help bend the K-wire 400 into position. In alternative embodiments, the K-wire 400 may not include driver tab 404, but instead a driver may engage the plate 402 directly for insertion.

The implant pins 410, 412 may have distal ends 414, 416 that are sharp, pointed, and/or chiseled so that they can be driven into the bone. The diameter of the implant pins 410, 412 will be sufficient to provide the structural strength and integrity for the implant pins 410, 412 to hold the fractured bone in place, but also to be able to be bent into a desired shape to be secured to the bone. In some embodiments, the implant pins 410, 412 may be of different lengths that may facilitate implanting the K-wire 400.

The plate 402 is attached between the driver tab 404 and the implant pins 410, 412. The plate 402 is shown as generally rectangular, but may take on other shapes as well. The plate 402 has a screw holes 406, 407 configured to receive screws to secure the plate 402 to the bone. Further, the holes 406, 407 may have frustoconical shaped rims 408, 409 that are configured to mate with the head of the screw used to secure the plate 402 to the bone. These rims 408, 409 facilitate a more secure fixation to the bone as well as leading to a lower profile installation as the screw head may be below the upper edge of the rims 408, 409. The plate 402 is designed to be as low profile as possible.

It is noted that in some situations while using the K-wires 100, 200 the bone fragment may rotate because of a single implant pin 112, 212. The K-wires 300, 400 use two implant pins which will prevent the rotation of the bone fragment when the K-wires 300, 400 are used.

Figure 3A:
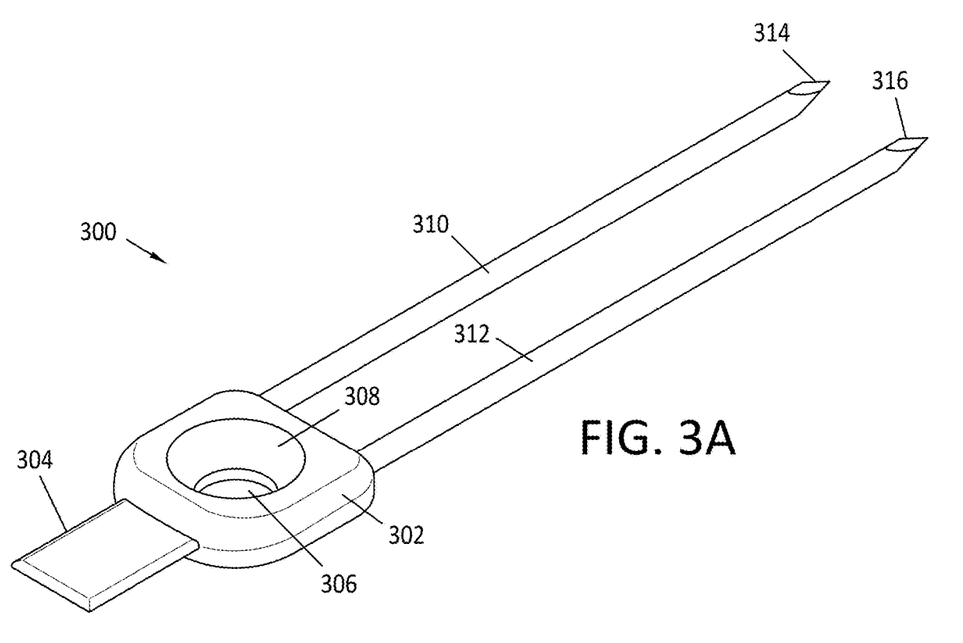
FIGS. 3A, 3B, 3C, 3D, and 3E illustrate perspective, top, side, end, and cross-sectional (through the plate) views respectively of a third embodiment of a K-wire with an integrated plate.
Figure 3B:
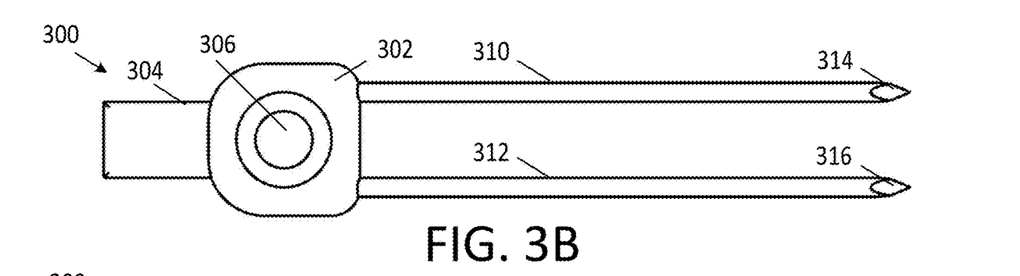
Figure 3C:
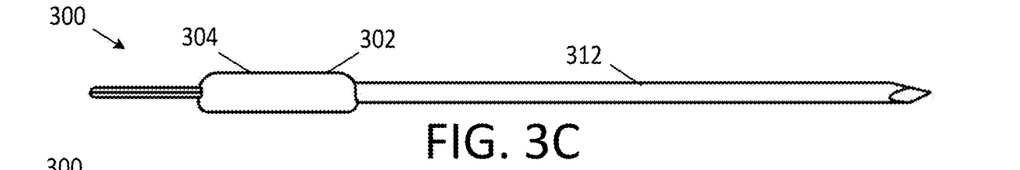
Figure 3D:
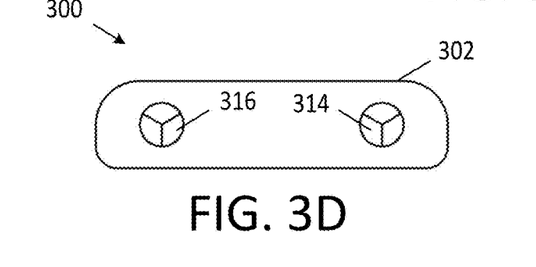
Figure 3E:
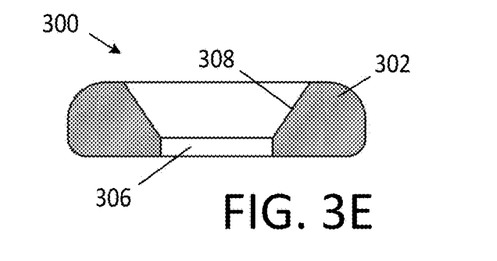
Figure 4A:
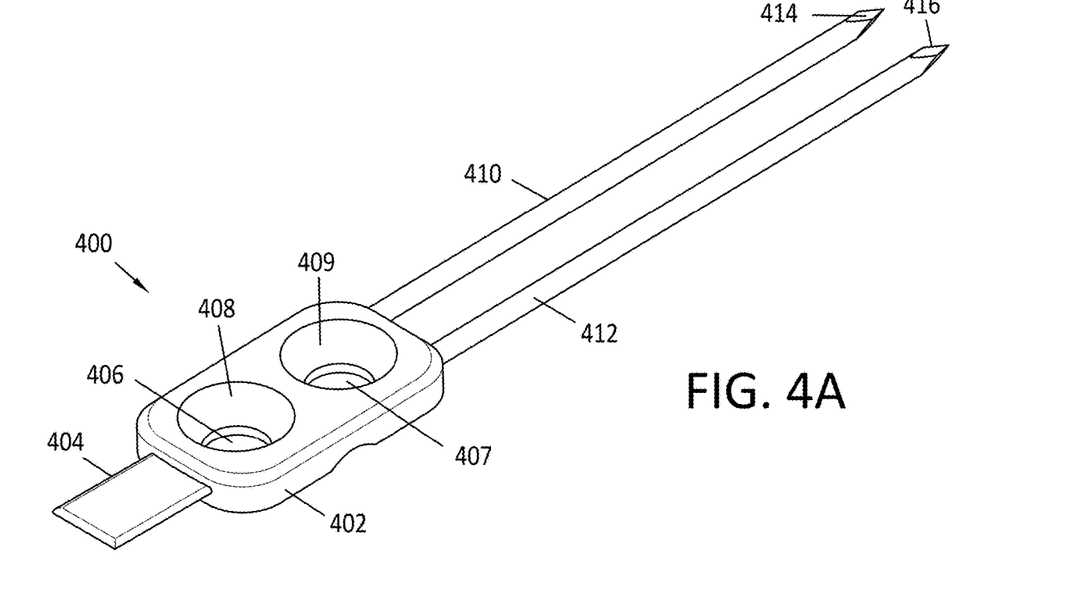
FIGS. 4A, 4B, 4C, 4D, and 4E illustrate perspective, top, side, end, and cross-sectional (through the plate) views respectively of a fourth embodiment of a K-wire with an integrated plate.
Figure 4B:
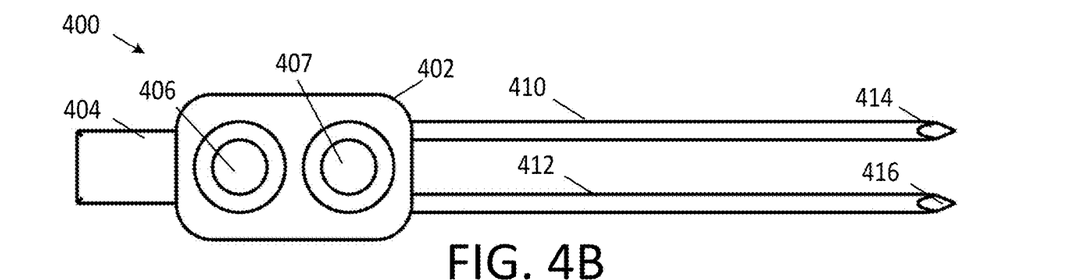
Figure 4C:
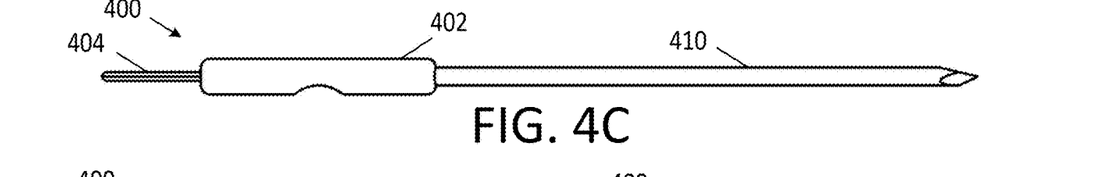
Figures 4D, 4E:
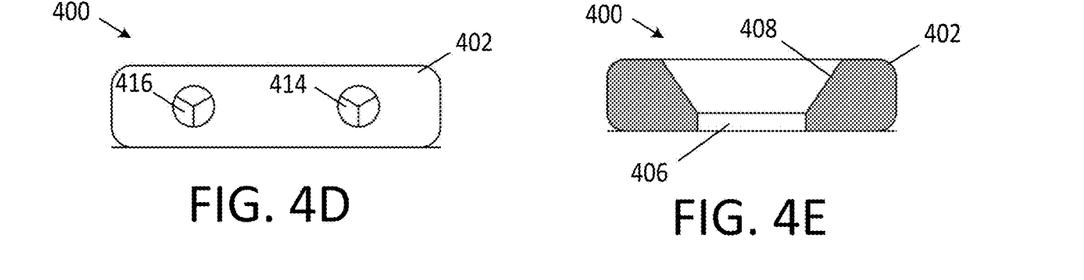
Figure 5A:
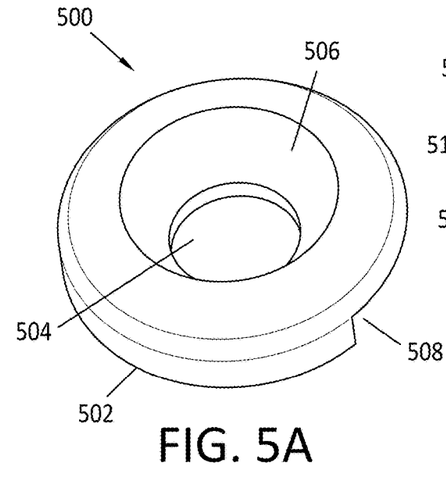
FIGS. 5A, 5B, 5C, 5D, and 5E illustrated top perspective, bottom perspective, top, cross-sectional, and side views respectively of a donut shaped washer.
Figure 5B:
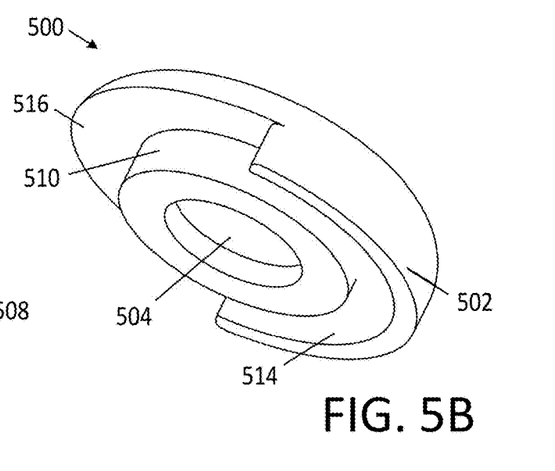
Figure 5C:
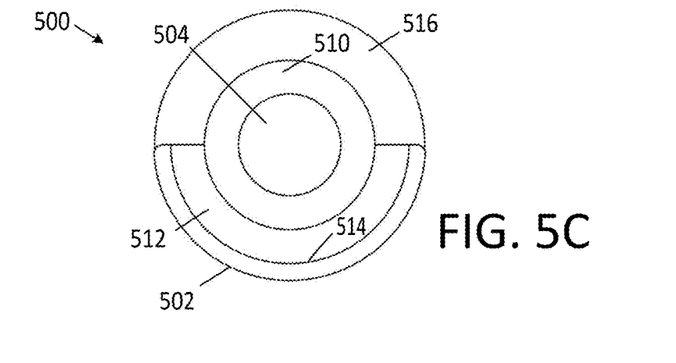
Figure 5D:
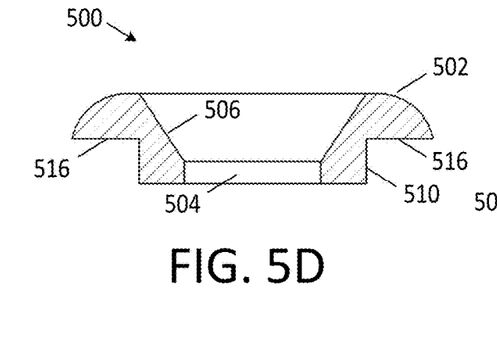
Figure 5E:
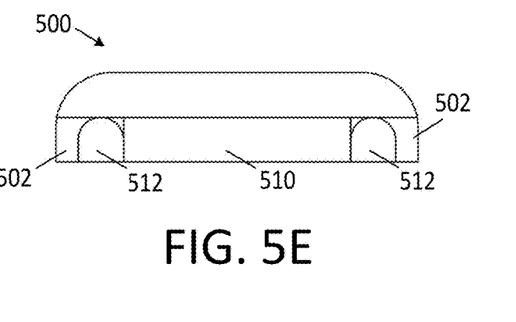
Figure 6A:
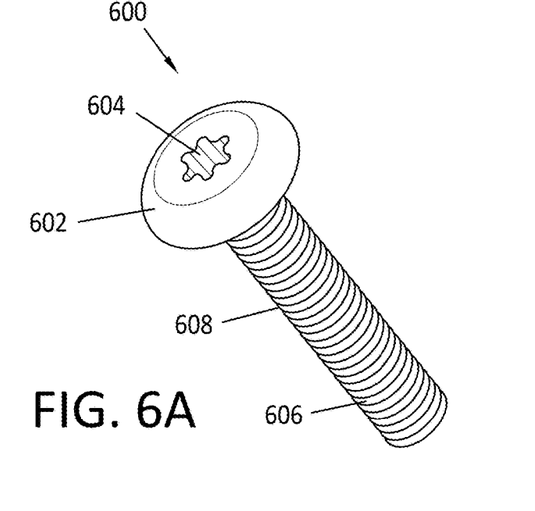
FIGS. 6A, 6B, 6C, 6D, and 6E illustrated top perspective, bottom perspective, side, cross-sectional, and top views of a screw with a channel.
Figure 6B:
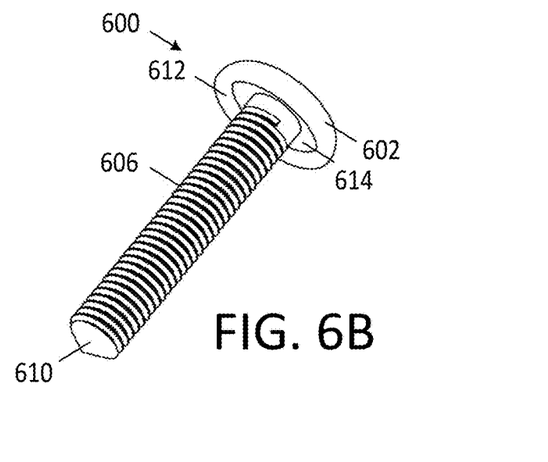
Figure 6C:
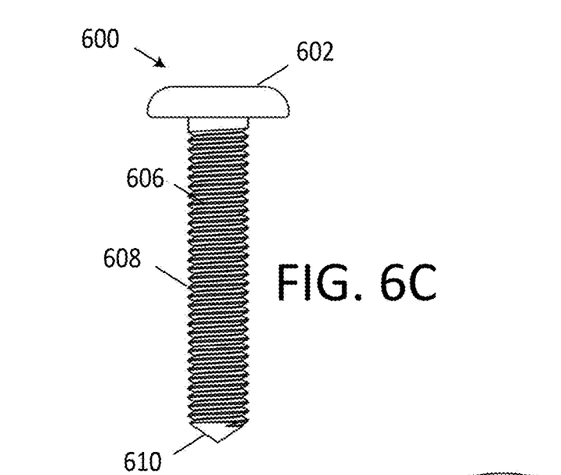
Figure 6D:
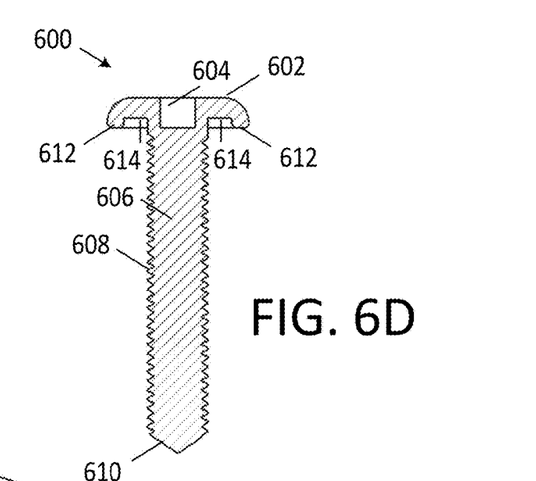
Figure 6E:
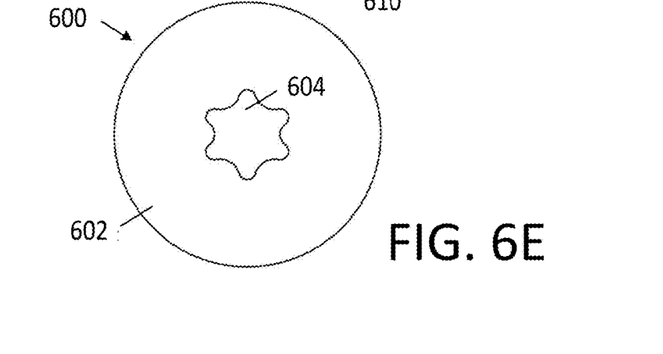

A method for using the K-wires 300, 400 will now be described. First, the bone fragment is reduced to the native bone. Next, two holes are drilled through the bone fragment into the native bone. This may be done using a regular K-wire or using a bone drill bit. The K-wire 300, 400 is then attached to a driver via either the driver tab 304, 404 or the plate 302, 402, and the K-wire 300, 400 is driven through the holes in bone fragment into the holes in the native bone. Then the K-wire 300, 400 may be backed out of the bone, for example by 5-10 mm. The K-wire 300, 400 is then bent to conform to the native bone so that the plate 302, 402 is flush to the native bone. Next, the bent K-wire 300, 400 is pushed back into the bone to be flush with the bone. The driver tab 304, 404 (if present) may then be cut off. Finally, a screw(s) is inserted into the plate 302, 402 to fix the plate 302, 402 and the K-wire 300, 400 to the bone.

A method for using the K-wires 300, 400 where the implantation pins are of different lengths will now be described. First, the bone fragment is reduced to the native bone. Next, two holes a drilled through the bone fragment into the native bone using regular K-wires. The K-wire 300, 400 is then attached to a driver via either the driver tab 304, 404 or the plate 302, 402. Then one of the regular K-wires is removed, and the longer implant pin is inserted into the hole. The additional length of the longer implant pin may be sufficient to extend into the native bone. Then the second regular K-wire is removed, and the K-wire 300, 400 is rotated so that the shorter implant pin aligns with the second hole, and then the shorter implant pin and hence the whole K-wire 300, 400 is driven into the bone fragment and the native bone. Then the K-wire 300, 400 may be backed out of the bone, for example by 5-10 mm. The K-wire 300, 400 is then bent to conform to the native bone so that the plate 302, 402 is flush to the native bone. Next, the bent K-wire 300, 400 is pushed back into the bone to be flush with the bone. The driver tab 304, 404 (if present) may then be cut off. Finally, a screw(s) is inserted into the plate 302, 402 to fix the plate 302, 402 and the K-wire 300, 400 to the bone. This approach allows for the bone fragment to remain securely in place at all times by at least one K-wire/implant pin.

This procedure may also use a single regular K-wire that is used to drill a first hole and then is used to drill the second hole and is left in place. Then the longer implant pin may be placed in the first hole and the procedure is then carried out as described above.

The K-wire embodiments described above may be used in a variety of applications and locations. The K-wires would be sized based upon the specific application and location. Further, because of the small area taken up by the plates, they leave ample area for other implants to be placed as needed to repair a bone fracture.

Various types of screws may be used with the K-wires embodiments include locking and variable angle screws if the application requires such screws. Accordingly, the screw holes would be modified to accommodate these other types of screws.

FIGS. 5A, 5B, 5C, 5D, and 5E illustrated top perspective, bottom perspective, top, cross-sectional, and side views respectively of a donut shaped washer. The donut shaped washer 500 includes a screw hole 504 and frustoconical rim 506 that are configured to accept a screw. The screw hole 504 is surrounded by a wall 510. The donut shaped washer 500 includes a rim 502 that extends from a lower surface 516 of the donut washer. The rim 502 extends around portion of the circumference of the donut washer 500. The rim 502 has an inner wall 514. The inner wall 514 of the rim 502, the wall 510, and the lower surface 516 form a channel 512. When the donut washer 500 is attached to a bone, an opening 508 is formed between the donut washer 500 and the bone. This opening will allow a K-wire to extend under the donut washer 500 into the channel 512.

The donut shaped washer 500 may be used to secure a K-wire to a bone. First, the bone fragment is reduced to the native bone. The K-wire is then attached to a driver, and the K-wire is driven through the bone fragment into the native bone. Then the K-wire may be backed out of the bone, for example by 5-10 mm. The K-wire is then bent to conform to the native bone. Next, a location for securing the K-wire to the native bone is selected. A tool may then be used to bend the K-wire at a location corresponding the location selected on the native bone. The tool bends the K-wire into a shape that corresponds to the channel 512 in the donut washer 500. The excess length of the bent K-wire may then be cut off so that the end of cut K-wire is in the channel 512 or at least under the lower surface 516. This will prevent a sharp end of the cut K-wire from causing soft tissue irritation to the patient. Then the donut washer 500 is placed over the cut K-wire, and a screw is placed through the screw hole 504 to compress the donut washer 500 and K-wire to the bone. The K-wire enters through the opening 508 and wraps around the donut washer 500.

FIGS. 6A, 6B, 6C, 6D, and 6E illustrated top perspective, bottom perspective, side, cross-sectional, and top views of a screw with a channel. The screw 600 includes a head 602 and a shank 606. The shank 606 has threads 608 and a distal end 610.

The head may include a drive 604 which in this example is star-shaped, but may take on other shapes as well. The underside of the head 602 includes a channel 614. The channel 614 is formed between a rim 612 and the shank 606. The channel 614 is configured to capture and secure a K-wire.

The screw with a channel 600 may be used to secure a K-wire to a bone. First, the bone fragment is reduced to the native bone. The K-wire is then attached to a driver, and the K-wire is driven through the bone fragment into the native bone. Then the K-wire may be backed out of the bone, for example by 5-10 mm. The K-wire is then bent to conform to the native bone. Next, a location for securing the K-wire to the native bone is selected. A tool may then be used to bend the K-wire at a location corresponding the location selected on the native bone. The tool bends the K-wire into a shape that corresponds to the channel 614 in the screw 600. The excess length of the bent K-wire may then be cut off so that the end of cut K-wire is in the channel 614. This will prevent a sharp end of the cut K-wire from causing soft tissue irritation to the patient. Then a hole may be drilled for the screw 600. The screw 600 may then be placed the through the bend in the K-wire and the screw tightened to compress the K-wire to the bone. The K-wire is mostly compressed to the bone by the channel 614 except where the K-wire passes under the rim 612 into the channel 614. The use of the channel 614 allows for the screw 600 to secure the K-wire to the native bone with a lower profile, because with the K-wire in the channel 614 the top of the head of screw may be tightened to be closer to the bone than without the channel. Further, compression of the bone surface may occur where the K-wire contacts the bone under the screw head 602, but this compression is minimized to just the point where the K-wire passes under the rim 612. One benefit of the screw 600 for securing a K-wire is that it is a single part leading to a less complicated insertion of the K-wire.

FIGS. 7A, 7B, 7C, and 7D illustrate perspective, top, side, and cross-sectional views of a slotted washer. The slotted washer 700 has a folded structure with an upper arm 710 and a lower arm 712. A connector 702 at an edge of the slotted washer 700 connects the upper arm 710 to the lower arm 712. There is a gap 714 between the upper arm 710 and the lower arm 712. The slotted washer 700 also includes a K-wire opening 708 adjacent the connector 702. The K-wire opening may be somewhat cylindrical in shape and is configured to receive an end of the K-wire therethrough. The upper arm 710 and lower arm 712 may have a screw hole 704. Further, the upper arm 710 may include a frustoconical shaped rim 706 that is configured to mate with the head of the screw used to secure the slotted washer 700 the bone. In some embodiments this rim 706 may extend into the lower arm 712 as well. The slotted washer 700 includes a window 716. The window 716 allows for the surgeon to see the location of the end of the K-wire through the K-wire opening 708.

Figures 7A, 7B:
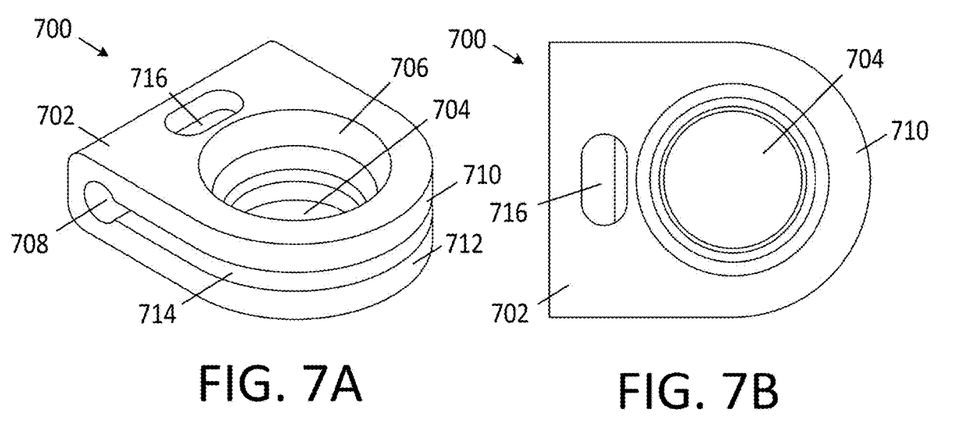
FIGS. 7A, 7B, 7C, and 7D illustrate perspective, top, side, and cross-sectional views of a slotted washer.
Figures 7C, 7D:
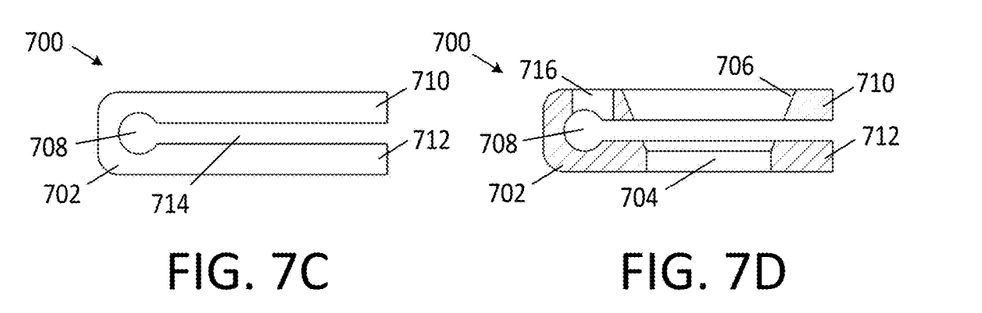
Figure 7E:
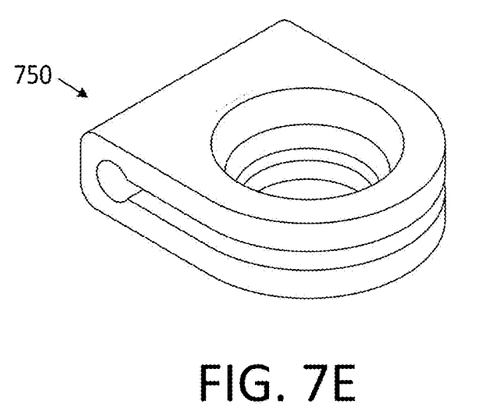
FIG. 7E illustrates a perspective view of another embodiment of the slotted washer without a window.

FIG. 7E illustrates a perspective view of another embodiment of the slotted washer 700 without a window.

The slotted washer 700 may be used to secure a K-wire to a bone. First, the bone fragment is reduced to the native bone. The K-wire is then attached to a driver, and the K-wire is driven through the bone fragment into the native bone. Then the K-wire may be backed out of the bone, for example by 5-10 mm. The K-wire is then bent to conform to the native bone. Next, a location for securing the K-wire to the native bone is selected. The excess length of the bent K-wire may then be cut off so that the end of cut K-wire ends up within the K-wire opening 708. This will prevent a sharp end of the cut K-wire from causing soft tissue irritation to the patient. Then the K-wire opening 708 of the slotted washer 700 is slid over the cut K-wire and a screw is placed through the screw hole 704 to compress the upper arm 710 towards the lower arm 712 which compresses and secures the K-wire in the K-wire opening 708. The screw also secures the slotted washer 700 and the K-wire to the bone. In the second embodiment of the slotted washer 700 of FIG. 7E, the surgeon may view the cut end of the K-wire as it passes through the window 716 to verify the location of the cut end of the K-wire. This ensures that the K-wire is inserted far enough into the slotted washer 700 and to ensure that the cut end of the K-wire does not stick out of the slotted washer 700 where it might cause irritation to the patient.

Because the K-wire does not need to be bent with the slotted washer, there is less handling of the K-wire while it being secured to the native bone. This reduces the possibility that the bone fragments are undesirably displaced or further broken.

The k-wire 100, k-wire 200, donut washer 500, screw 600, and slotted washer 700 each allow for increased flexibility as to where the K-wire is secured to native bone. Each also provides a low profile solution as well as taking up a small area on the bone to allow room for other implants to be used to treat the fracture as needed.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A method for implanting a K-wire using a slotted washer, wherein the slotted washer comprises;
   an upper arm with a first screw hole;
   a lower arm with a second screw hole;
   a connector connecting the upper arm with the lower arm; and
   a K-wire opening configured to receive and compress the K-wire, the K-wire opening disposed adjacent the connector and between the lower arm and upper arm;
the method comprising:
   reducing a bone fragment to a native bone;
   driving the K-wire through the bone fragment into the native bone;
   backing the K-wire out of the bone;
   bending the K-wire to conform to the native bone so that the slotted washer is flush to the native bone;
   pushing the bent K-wire back into the bone;
   selecting a location to secure the K-wire to the native bone;
   cutting off an excess length of the K-wire;
   placing the slotted washer over the cut K-wire; and
   inserting a screw through the first screw hole and the second screw hole to secure the slotted washer and the K-wire to the native bone.

2. The method of claim 1, wherein the slotted washer further comprises a window adjacent the K-wire opening configured to provide a view of the K-wire during insertion into the K-wire opening.

3. The method of claim 2, wherein the window is in the upper arm.

4. The method of claim 2, wherein the window is in the upper arm and the lower arm.

5. The method of claim 2, further comprising positioning the slotted washer along the K-wire so that an end of the K-wire is visible in the window.

6. The method of claim 2, further comprising positioning the slotted washer along the K-wire so that the K-wire extends through the window.

7. The method of claim 1, wherein the first screw hole of the upper arm includes a frustoconical shaped rim.

8. The method of claim 1, wherein a width of the K-wire opening is greater than a width of a gap between the upper arm and the lower arm.

9. The method of claim 1, wherein an upper surface of the slotted washer is substantially planar.

* * * * *